(12) United States Patent
Bischoff et al.

(10) Patent No.: US 8,219,211 B2
(45) Date of Patent: *Jul. 10, 2012

(54) INSULATING MEMBER FOR A MEDICAL ELECTRICAL LEAD AND METHOD FOR ASSEMBLY

(75) Inventors: Thomas C. Bischoff, Minneapolis, MN (US); Kathryn R. Parsons, Fridley, MN (US); Marc R. Helmick, Newton, MA (US); Bret R. Shobert, Corcoran, MN (US); George M. Huepenbecker, Vadnais Heights, MN (US); Sandra F. Viktora, Coon Rapids, MN (US); James J. Snyder, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 179 days.

This patent is subject to a terminal disclaimer.

(21) Appl. No.: 12/481,216

(22) Filed: Jun. 9, 2009

(65) Prior Publication Data
US 2009/0240315 A1    Sep. 24, 2009

Related U.S. Application Data

(63) Continuation of application No. 10/124,802, filed on Apr. 17, 2002, now Pat. No. 7,546,163.

(60) Provisional application No. 60/284,430, filed on Apr. 17, 2001.

(51) Int. Cl.
*A61N 1/00* (2006.01)
(52) U.S. Cl. .................................................. 607/116
(58) Field of Classification Search .................. 607/116
See application file for complete search history.

(56) References Cited

U.S. PATENT DOCUMENTS

| | | | |
|---|---|---|---|
| 3,939,843 A * | 2/1976 | Smyth | 607/126 |
| 4,106,512 A | 8/1978 | Bisping | |
| 4,217,913 A | 8/1980 | Dutcher | |
| 4,784,161 A | 11/1988 | Skalsky et al. | |
| 4,886,074 A | 12/1989 | Bisping | |
| 5,246,014 A | 9/1993 | Williams et al. | |
| 5,275,171 A | 1/1994 | Barcel | |
| 5,425,755 A | 6/1995 | Doan | |
| 5,456,708 A | 10/1995 | Doan et al. | |
| 5,584,873 A | 12/1996 | Shoberg et al. | |
| 5,716,390 A | 2/1998 | Li | |
| 5,968,087 A | 10/1999 | Hess et al. | |
| 6,016,436 A | 1/2000 | Bischoff et al. | |
| 6,052,625 A | 4/2000 | Marshall | |
| 6,148,237 A | 11/2000 | Das | |
| 6,366,820 B1 | 4/2002 | Doan et al. | |
| 6,374,142 B1 | 4/2002 | Skinner et al. | |
| 6,813,521 B2 | 11/2004 | Bischoff et al. | |
| 6,931,285 B2 | 8/2005 | Bischoff | |
| 7,546,163 B2 | 6/2009 | Bischoff et al. | |
| 2002/0183822 A1 | 12/2002 | Bodner | |
| 2002/0188337 A1 | 12/2002 | Bischoff | |
| 2002/0188340 A1 | 12/2002 | Bischoff et al. | |

* cited by examiner

*Primary Examiner* — George Manuel
(74) *Attorney, Agent, or Firm* — Carol F. Barry

(57) ABSTRACT

A medical electrical lead that includes a lead body having a lead body lumen, an electrode head assembly fixedly engaged with the lead body and having an electrode head assembly lumen communicating with the lead body lumen, and a conductor extending within the lead body lumen and the electrode head assembly lumen. An insulating member extends through the electrode head assembly lumen and the lead body lumen to electrically isolate the conductor.

16 Claims, 4 Drawing Sheets

INSULATING MEMBER FOR A MEDICAL ELECTRICAL LEAD AND METHOD FOR ASSEMBLY

REFERENCE TO PRIORITY APPLICATION

This application is a continuation of U.S. patent application Ser. No. 10/124,802 filed on Apr. 17, 2002. The disclosure of the above application is incorporated herein by reference.

In addition, this application claims the benefit of U.S. Provisional Application No. 60/284,430, entitled "MEDICAL ELECTRICAL LEAD", incorporated herein by reference in its entirety.

CROSS-REFERENCE TO RELATED APPLICATIONS

Cross-reference is hereby made to commonly assigned related U.S. Applications, filed concurrently herewith, Ser. No. 10/124,185, entitled "DRIVE SHAFT SEAL FOR A MEDICAL ELECTRICAL LEAD"; Ser. No. 10/124,530, entitled "IMPLANTABLE MEDICAL LEAD HAVING A RETRACTION STOP MECHANISM"; Ser. No. 10/124,160, entitled "APPARATUS FOR TRANSFERRING TRACTION FORCES EXERTED ON AN IMPLANTABLE MEDICAL LEAD"; and Ser. No. 10/124,777, entitled "MEDICAL ELECTRICAL LEAD".

FIELD OF THE INVENTION

The present invention relates to medical electrical leads in general, and, more particularly, the present invention relates to maintaining electrical isolation between various electrodes and conductors of an implantable medical lead.

BACKGROUND OF THE INVENTION

A wide assortment of implantable medical devices (IMDs) are presently known and in commercial use. Such devices include cardiac pacemakers, cardiac defibrillators, cardioverters, neurostimulators, and other devices for delivering electrical signals to a portion of the body and/or receiving signals from the body. Pacemakers, for example, are designed to operate so as to deliver appropriately timed electrical stimulation signals when needed, in order to cause the myocardium to contract or beat, and to sense naturally occurring conduction signals in the patient's heart.

Devices such as pacemakers, whether implantable or temporary external type devices, are part of a system for interacting with the patient. In addition to the pacemaker device, which typically has some form of pulse generator, a pacing system includes one or more leads for delivering generated stimulation pulses to the heart and for sensing cardiac signals and delivering sensed signals from the heart back to the pacemaker. As is known, pacemakers can operate in either a unipolar or bipolar mode, and can pace the atria or the ventricles. Unipolar pacing requires a lead having only one distal electrode for positioning in the heart, and utilizes the case, or housing of the implanted device as the other electrode for the pacing and sensing operations. For bipolar pacing and sensing, the lead typically has two electrodes, a tip electrode disposed at the distal end of the lead, and a ring electrode spaced somewhat back from the distal end. Each electrode is electrically coupled to a conductive cable or coil, which carries the stimulating current or sensed cardiac signals between the electrodes and the implanted device via a connector.

In order to perform reliably, cardiac pacing leads need to be positioned and secured at a targeted cardiac tissue site in a stable manner. One common mechanism for securing an electrode position is the use of a rotatable fixation helix. The helix exits the distal end of the lead and can be screwed into the body tissue. The helix itself may serve as an electrode or it may serve as an anchoring mechanism to locate an electrode mounted to the lead body adjacent a targeted tissue site. The fixation helix may be coupled to a drive shaft that is further connected to a coiled conductor that extends through the lead body as generally described in U.S. Pat. No. 4,106,512 to Bisping et al. A physician rotates the coiled conductor at a proximal end to cause rotation of the fixation helix via the drive shaft. As the helix is rotated in one direction, the helix is secured in the cardiac tissue. Rotation in the opposite direction removes the helix from the tissue to allow for repositioning of the lead at another location.

Combination devices are available for treating cardiac arrhythmias that are capable of delivering shock therapy for cardioverting or defibrillating the heart in addition to cardiac pacing. Such a device, commonly known as an implantable cardioverter defibrillator or "ICD", uses coil electrodes for delivering high-voltage shock therapies. An implantable cardiac lead used in combination with an ICD may be a quadrapolar lead equipped with a tip electrode, a ring electrode, and two coil electrodes. A quadrapolar lead requires four conductors extending the length of the lead body in order to provide electrical connection to each electrode.

Pacemaker systems, as well as other medical devices such as those mentioned above, can utilize a wide variety of lead designs. Many considerations are taken into account when optimizing the design of a lead. For example, minimizing lead size is important since a smaller device is more readily implanted within the cardiac structures or coronary vessels of a patient. Electrical insulation between multiple conductors and their associated electrodes is crucial to providing the desired therapeutic effect of electrical stimulation. With the increased number of insulated conductors required in quadrapolar leads, the diameter of the lead body is increased. It is desirable, however, to minimize the lead body diameter while maintaining proper insulation and the structural integrity of the lead.

Moreover, providing features that make a lead easier to implant and extract allows the clinician to complete the associated surgical procedure more safely and in less time. Finally, an optimized lead design is ideally manufactured using techniques that are relatively simple and easy to verify. The resulting product should be easy to test so that manufacturing defects can be detected prior to the implant of the device within a patient. What is needed, therefore, is an improved lead design that takes all of the foregoing factors into account, thereby providing a device that can be safely and efficiently deployed, used, and, if necessary, extracted.

SUMMARY OF THE INVENTION

The present invention is realized by providing a medical electrical lead that includes a lead body having a lead body lumen, an electrode head assembly fixedly engaged with the lead body and having an electrode head assembly lumen communicating with the lead body lumen, and a conductor extending within the lead body lumen and the head assembly lumen. An insulating member extends through the electrode head assembly lumen and the lead body lumen, electrically isolating the conductor.

In a preferred embodiment, the insulating member is formed from polytetrafluoroethylene (PTFE). The PTFE member can be made thinner than other polymers that might be used for insulation allowing the overall lead body diameter to be minimized. The PTFE member further provides a low-interference and low-friction surface for the rotation of the coiled conductor during advancement or retraction of the helical tip electrode.

The insulating member is preferably etched or otherwise treated to enhance an adhesive bond between the insulating member and the electrode head assembly, which houses a tip electrode. The bond between the insulating member and the electrode head assembly enables the lead body to be coupled to the electrode head assembly at a butt joint, simplifying manufacturing processes. The bond between the insulating member and the electrode head assembly, which is preferably fabricated from polyurethane, provides strain relief to the conductor during lead implantation or extraction. The insulating member provided in accordance with the present invention thus provides proper insulation using a minimal amount of space and further allows a strengthening bond between modular components of a medical lead.

Another aspect of the present invention is a method for assembling a medical electrical lead that includes fixedly engaging an insulating member, for electrically isolating a conductor, within a first lumen at a proximal end of an electrode head assembly, inserting the insulating member within a second lumen of a distal end of a lead body, and fixedly engaging the proximal end of the electrode assembly and the distal end of the lead body.

DETAILED DESCRIPTION OF THE INVENTION

Figure 1:
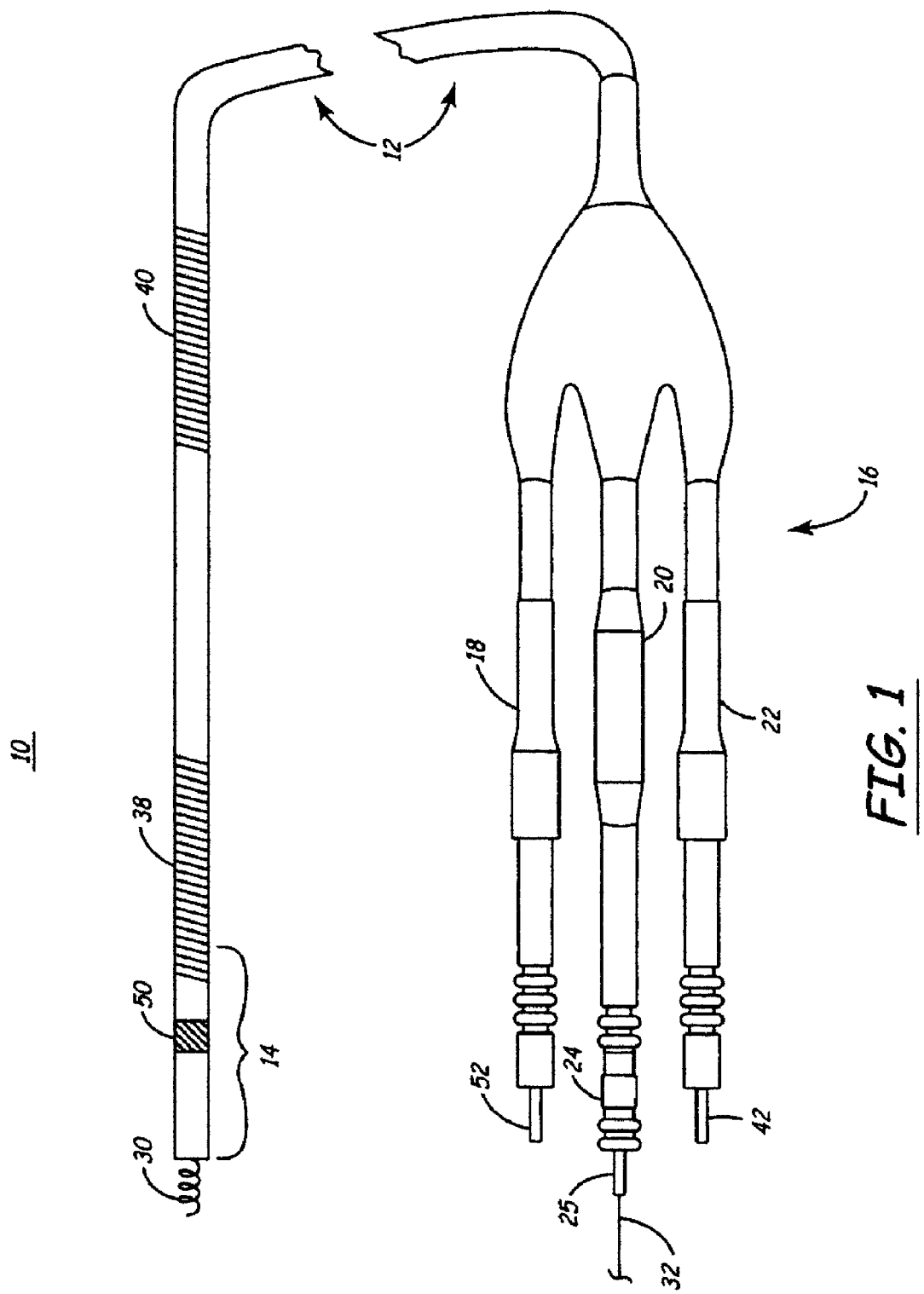
FIG. 1 is a plan view of an implantable cardiac lead that may be utilized in accordance with the present invention.

FIG. 1 is a plan view of an implantable cardiac lead that may be used in accordance with the present invention, embodied as a transvenous cardiac defibrillation lead. As illustrated in FIG. 1, a lead 10 includes an elongated lead body 12 having a connector assembly 16 at a proximal end of the lead 10 for connecting to an implantable device, and an electrode head assembly 14 at a distal end of the lead 10 for carrying one or more electrodes. Lead 10 is shown as a quad-rapolar lead including, at or near the distal end, a helical tip electrode 30, a ring electrode 50, a right ventricular (RV) defibrillation coil 38 and a superior vena cava (SVC) defibrillation coil 40. The helical tip electrode 30 and ring electrode 50 may be utilized to sense cardiac signals and/or deliver pacing pulses to a patient. One of the defibrillation coils 38 or 40 serves as the cathode while the other serves as the anode during delivery of a defibrillation shock to a patient as a result of a detected tachycardia or fibrillation condition.

The lead body 12 takes the form of an extruded tube of biocompatible plastic such as silicone rubber. Multiple lumens located within the lead body 12, carry four insulated conductors from the connector assembly 16 to the corresponding electrodes 30, 50, 38 and 40 located at or near the distal end of the lead 10. The multi-lumen lead body 12 may correspond generally to that disclosed in U.S. Pat. No. 5,584,873 issued to Shoberg et al., incorporated herein by reference in its entirety. Three of the insulated conductors carried by lead body 12 are stranded or cabled conductors, each electrically coupled to one of the ring electrode 50, RV coil 38 and SVC coil 40. The cabled conductors may correspond generally to the conductors disclosed in U.S. Pat. No. 5,246,014, issued to Williams et al., incorporated herein by reference in its entirety. A fourth, coiled conductor extends the length of the lead body 12 and is coupled to the helical tip electrode 30.

In this embodiment, the helical tip electrode 30 functions as an electrode for cardiac pacing and/or sensing and as an active fixation device for anchoring the lead 10 in a desired position. In other embodiments that may employ aspects of the present invention, a helical tip may function only as an active fixation device. Reference is made to U.S. Pat. No. 4,217,913 to Dutcher, incorporated herein by reference in its entirety. Therefore, the helical tip electrode 30 may also be referred to herein as a "fixation helix."

The connector assembly 16 has multiple connector extensions 18, 20, and 22 arising from a trifurcated connector sleeve, typically formed of silicone rubber. The connector extensions 18, 20, and 22 couple the lead 10 to an implantable medical device such as an implantable cardioverter defibrillator (ICD).

Connector extension 20 is shown as a bi-polar connector including a connector ring 24 and a connector pin 25. Connector extension 20 houses the cabled conductor that is electrically coupled to the connector ring 24 at its proximal end and to the ring electrode 50 at its distal end. The connector extension 20 also houses the coiled conductor that is electrically coupled to the connector pin 25 and extends to the tip electrode 30. During a lead implant or explant procedure, rotation of the connector pin 25 relative to the connector assembly 16 causes corresponding rotation of the coiled conductor and advancement or retraction of the helical tip electrode 30 in the fashion generally described in U.S. Pat. No. 4,106,512 to Bisping et al., incorporated herein by reference in its entirety. By advancing the tip electrode 30, the electrode 30 can be actively fixed in cardiac tissue. A stylet 32 may be advanced within an inner lumen of the coiled conductor to the distal end of the lead 10 to aid in lead placement during an implant procedure.

The connector extension 18 carries a single connector pin 52 that is electrically coupled to an insulated cable extending the length of the lead body 12 and electrically coupled to the RV coil 38. The connector extension 22 carries a connector pin 42 that is electrically coupled to a respective insulated cable that is further coupled to the SVC coil 40.

Figure 2:
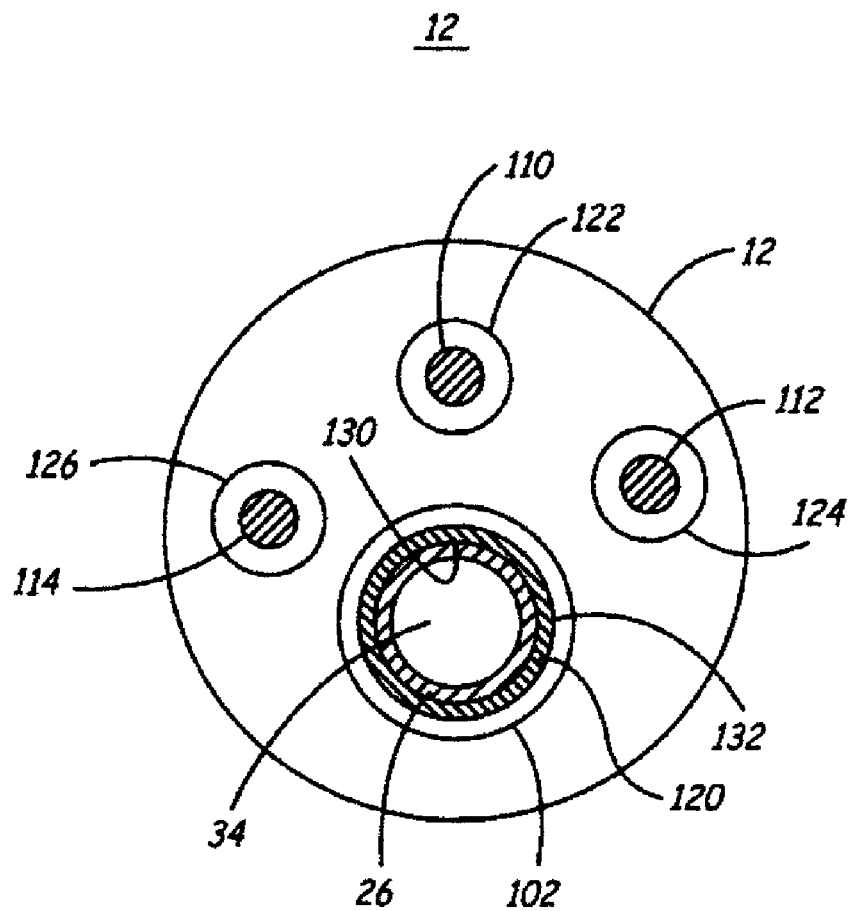
FIG. 2 is a cross-sectional view of a multi-lumen lead body of the lead shown in FIG. 1.

FIG. 2 is a cross-sectional view of a multi-lumen lead body of the lead of FIG. 1. As illustrated in FIG. 2, the lead body 12 includes four lumens 102, 122, 124, and 126. Lumen 102 carries the coiled conductor 26 that is coupled to the helical tip electrode 30. In accordance with the present invention, the conductor 26 is shown surrounded by insulation tubing 120. A stylet 32 may be advanced within the lumen 34 of the coiled conductor 26. Lumen 122 carries an insulated cable 110 that is electrically coupled at a proximal end to the connector ring 24 and at a distal end to the ring electrode 50. Lumen 124 carries an insulated cable 112 that is electrically coupled at a proximal end to the connector pin 52 and at a distal end to the RV coil 38. Lumen 126 carries an insulated cable 114 that is electrically coupled at a proximal end to the connector pin 42 and at a distal end to the SVC coil 40.

Figure 3:
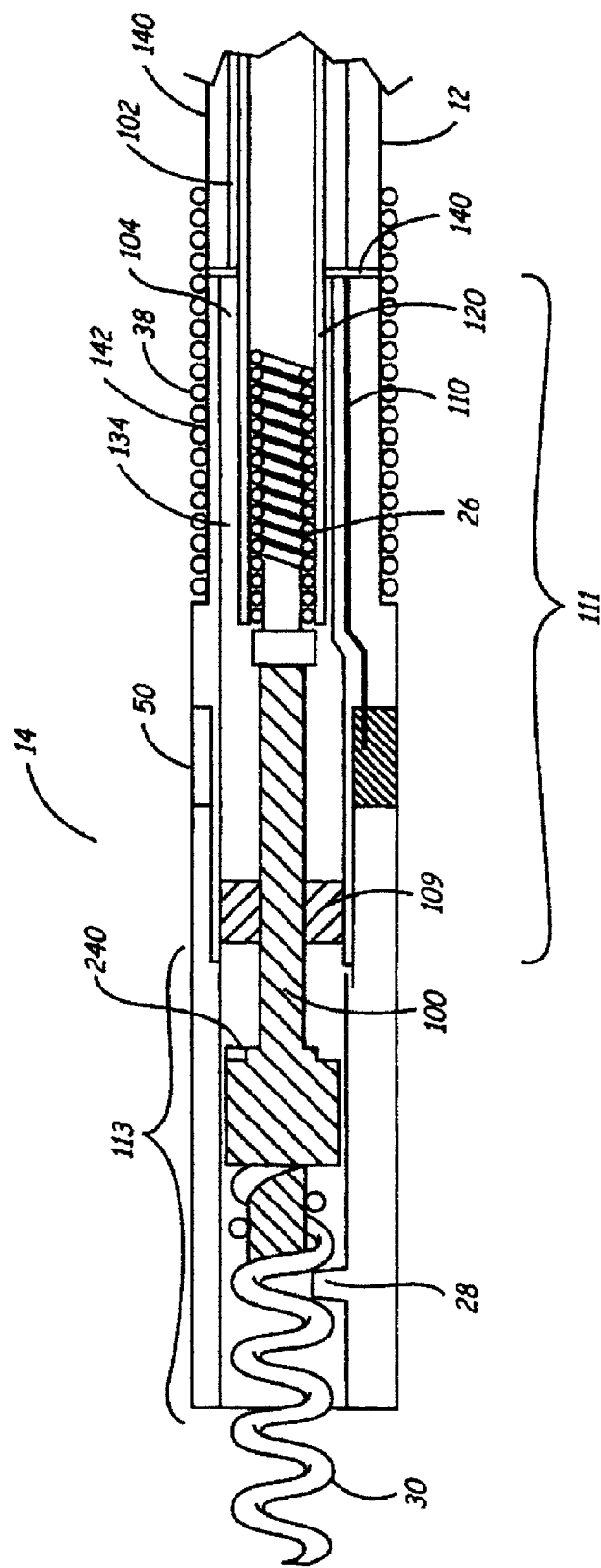
FIG. 3 is a side, cut-away view of a distal end of the lead shown in FIG. 1.

FIG. 3 is a side cutaway view of the distal end of the lead 10 showing a detailed view of the electrode head assembly 14 and the electrodes 30, 50 and 38. The molded, tubular electrode head assembly 14 includes two members, a distal electrode head assembly 113 and a proximal electrode head assembly 111. The distal and proximal electrode head assemblies 113 and 111 are preferably formed from a relatively rigid biocompatible plastic. For example, assemblies 113 and 111 may be fabricated from molded polyurethane. The proximal electrode head assembly 111 is coupled to the multi-lumen lead body 12, typically formed from a relatively more compliant plastic such as silicone rubber, at a joint 140. The lumen 104 within the proximal electrode head assembly 111 communicates with the lumen 102 within the lead body 12 for carrying the coiled conductor 26 extending between the tip electrode 30 and the connector ring 24. In FIG. 3, the ring electrode 50 is shown coupled to the cable 110, and the RV coil 38 is shown positioned on the outer diameter of the proximal electrode head assembly 111 and the lead body 12.

FIG. 3 further shows the helical tip electrode 30 electrically coupled to the coiled conductor 26 via a drive shaft 100. One particular advantage of fabricating the electrode head assembly 14 from polyurethane components is that polyurethane components may be made transparent. This transparency allows for inspection of the weld that affixes helical tip electrode 30 to the distal end of the drive shaft 100 so that lead integrity is better verified. The electrode 30 and drive shaft 100 are preferably fabricated of a biocompatible metal such as platinum iridium alloy. The coiled conductor 26 extends to the proximal connector assembly 16. Rotation of the connector pin 25 at the proximal end of coiled conductor 26 causes corresponding rotation of the distal end of the coiled conductor 26 to, in turn, cause rotation of the drive shaft 100. This rotation results in extension or retraction of helical tip electrode 30. A guide 28 actuates the helical tip 30 as it is advanced or retracted. The lead 10 may include a drive shaft seal 109 encircling the drive shaft 100. The drive shaft seal 109, which may be formed of silicone or any other elastomer, is housed within the proximal electrode head assembly 111.

One problem with quadrapolar leads involves maintaining electrical isolation between the various electrodes and conductors in the system. For example, when delivering pacing pulses to a patient, current is ideally supplied via coiled conductor 26 and helical tip electrode 30 to body tissue surrounding the tip electrode 30. Most of this current then travels through the body tissue back to ring electrode 50 and is then carried back to the implantable device via the cable 110. However, if electrical isolation is not maintained between the coiled conductor 26 and the RV coil 38, current may travel from the RV coil 38 to the coiled conductor 26 when high-energy defibrillation shocks are delivered, potentially injuring tissue in contact with the helical tip electrode 30.

The current invention utilizes an insulating member, such as a thin insulation tube 120, to electrically isolate the coiled conductor 26 from RV coil 38 and ring electrode 50. The insulation tube 120 extends from the lumen 104 within the proximal electrode head assembly 111, through the lumen 102 within the lead body 12, to the connector assembly 16. The insulation tube 120 is preferably a polymer having a high dielectric strength such as PTFE or ethyl tetrafluoroethylene (ETFE). The properties of PTFE are particularly suited for functioning as the insulation tubing around coiled conductor 26 because PTFE can be made into a tube with a smaller diameter and thinner wall than other polymers, such as silicone rubber or urethane, allowing overall lead size to be minimized. Furthermore, the PTFE tubing provides a low-interference and low-friction interface with the coiled conductor 26, which must easily rotate within the insulation tube 120 in order to advance or retract the fixation helix 30.

As illustrated in FIGS. 2 and 3, an inner lumen 130 of insulation member tube 120 houses coiled conductor 26, and prevents current leakage between the coiled conductor 26, RV coil 38 and ring electrode 50. In a preferred embodiment of the invention, an outer surface 132 of the insulation tube 120 is bonded to an inner surface 134 of lumen 104 within the proximal electrode head assembly 111 using an epoxy, polyurethane or other adhesive. Urethane adhesive is preferred because it is readily applied using a solvent, making the manufacturing process more efficient. The outer surface 132 of the insulation tubing 120 is preferably etched to facilitate bonding with adjacent components, such as the inner surface 134 of lumen 104. Additionally, the polyurethane adhesive provides an improved bond between PTFE insulation tube 120 and the urethane walls surrounding the lumen 104 over silicone adhesives. The ability to form a complete seal further prevents current leakage between the distal end of coiled conductor 26, RV coil 38, and ring electrode 50.

By bonding the insulation tubing 120 to the proximal electrode head assembly 111, a modular lead design is possible in which the proximal electrode head assembly is joined to the lead body 12 at the butt joint 140 shown in FIG. 3.

Figure 4:
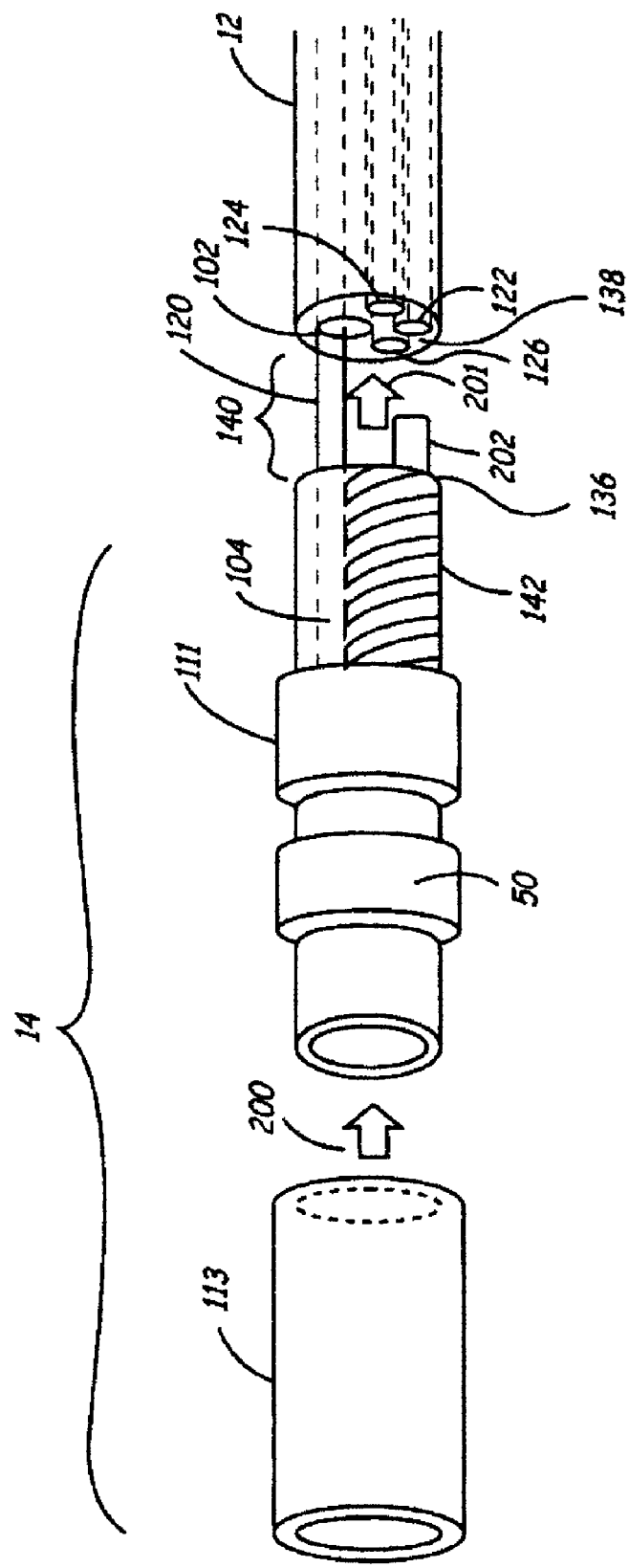
FIG. 4 is a perspective view of the modular components used in assembling the distal end of the lead shown in FIG. 3.

FIG. 4 is a perspective view illustrating the modularity that may be provided by the electrode head assemblies 111 and 113 and the multi-lumen lead body 12 with use of the insulation tubing 120. Arrows 200 and 201 show the manner in which the distal and proximal electrode head assemblies 113 and 111 are joined together and with lead body 12. According to one method of assembling this lead 10, the insulation tubing 120 may be inserted into lumen 104 of the proximal electrode head assembly 111 and bonded thereto using, for example, a urethane adhesive. Next, the unbonded proximal end of the insulation tubing 120 may be inserted into lumen 102 at the distal end of the lead body 12. A bonding process may then be utilized to bond a proximal end 136 of the proximal electrode head assembly 111 to a distal end 138 of the silicone lead body 12 at butt joint 140 so that the proximal end 136 is fixedly positioned adjacent to the distal end 138. For example, a silicone adhesive may be used to facilitate this bonding of the proximal end 136 to the distal end 138. The insulation tubing 120 provides mechanical stability, electrical isolation, added lead body strength, and improved flex life in the vicinity of the butt joint 140.

The assembly of lead 10 may also include bonding the RV coil 38 to an outer portion 140 of the lead body 12 and an outer portion 142 of the proximal electrode head assembly 111, as in the position shown in FIG. 3. The grooved area 142 of assembly 111 provides an adhesive grip and aids in holding the RV coil 38 in place. The placement of RV coil 38 across the butt joint 140 provides additional stability to the joint 140. The ring electrode 50 is captured in the position shown in FIG. 3 between the distal electrode head assembly 113 and the proximal electrode head assembly 111 after they are joined. The cabled conductor 110 coupled to the ring electrode 50 (FIG. 3) provides additional stress relief to the butt joint 140.

FIG. 4 further shows an optional electrode head peg 202 used in conjunction with lumen 126 to provide alignment of the proximal electrode head assembly 111 and the lead body 12 during the manufacturing process. As shown previously in FIG. 2, the lumen 126 houses the cable 114 (shown in FIG. 2) that extends from connector assembly 16 to the SVC coil 40. Distal to the SVC coil 40, the lumen 126 is empty, advantageously providing a port at the distal end of the lead body 12 in which to engage the electrode head peg 202. The electrode head peg 202 may be bonded within lumen 126 using an adhesive, preferably a silicone adhesive, to provide additional strength and strain relief to the butt joint 140.

The modular assembly provided by the embodiments of the invention described above provides several advantages.

The assembly method allows the proximal and distal electrode head assemblies 111 and 113 to be manufactured separately and coupled to the lead body 12 later in the manufacturing process. The modular design makes the electrode head assemblies 111 and 113 easier to inspect and test, and also simplifies the lead assembly process. By utilizing the insulation tubing 120, a method for joining a polyurethane electrode head assembly 14 and a silicone lead body 12 in a stable, reliable manner can be realized without increasing the lead diameter at the joint or requiring difficult manufacturing processes. It may further be noted that the RV defibrillation coil 38 and the optional electrode head peg 202 provide additional strain relief at the butt joint 140.

The lead described above with respect to the current inventive lead system is a quadrapolar high-voltage lead of the type that may be used in conjunction with an implantable cardioverter defibrillator. However, it will be understood by one skilled in the art that any or all of the inventive aspects described herein may be incorporated into other types of lead systems. For example, one or more of the aspects may be included in a unipolar or multipolar pacing lead. An alternative lead design may include any combination of a tip electrode, one or more ring electrodes, or one or more coil electrodes for use in pacing, sensing, and/or shock delivery. Alternatively, drug-delivery or other electrical stimulation leads may employ aspects of the current inventive lead system for minimizing lead diameter, ensuring reliability, and simplifying assembly and testing methods. As such, the above disclosure should be considered exemplary, rather than limiting, with regard to the following claims.

We claim:

1. A medical electrical lead, comprising:
   a lead body defining at least a first lead body lumen, the lead body extending between a distal end and a proximal end;
   a connector assembly at the proximal end of the lead body;
   an electrode head assembly extending between a proximal end, fixedly engaged with the distal end of the lead body and forming a joint therewith, and a distal end, wherein the electrode head assembly comprises at least one electrode, and further wherein a body of the electrode head assembly extending between the distal end and the proximal end defines an electrode head assembly lumen communicating with the lead body lumen when the electrode head assembly is fixedly engaged with the distal end of the lead body;
   at least a first conductor extending within the first lead body lumen and the electrode head assembly lumen; and
   an insulating member, extending across the joint through at least a portion of the electrode head assembly lumen defined by the body of the electrode head assembly and through at least a portion of the first lead body lumen, electrically isolating the conductor.

2. The medical electrical lead of claim 1, wherein the insulating member is formed of a polymer having a high dielectric strength.

3. The medical electrical lead of claim 2, wherein the insulating member is formed of PTFE tubing.

4. The medical electrical lead of claim 1, further comprising a coil and an electrode, wherein the insulating member prevents current leakage between the first conductor and at least one of the coil and the electrode.

5. The medical electrical lead of claim 4, wherein the insulation member comprises an outer surface and the electrode head assembly lumen defines an inner surface, wherein the outer surface of the insulation member is bonded to the inner surface of the electrode head assembly lumen.

6. The medical electrical lead of claim 5, wherein the outer surface of the insulation member is etched.

7. The medical electrical lead of claim 5, wherein the proximal end of the electrode head assembly is fixedly positioned adjacent to the distal end of the lead body to form a butt joint.

8. The medical electrical lead of claim 7, wherein the coil is fixedly engaged with and about at least a portion of the lead body and about at least a portion of the body of electrode head assembly across the joint, and wherein the body of the electrode head assembly includes a grooved portion fixedly engaging the coil.

9. The medical electrode lead of claim 7, further comprising:
   a protruding member extending from the proximal end of the electrode head assembly; and
   an engaging portion positioned at the distal end of the lead body receiving the protruding member to align the electrode head assembly with the lead body.

10. The medical electrode lead of claim 9, further comprising:
    a second lead body lumen extending from the proximal end of the lead body to the distal end of the lead body;
    an electrode positioned along the lead body; and
    a second conductor extending through the second lead body lumen from the proximal end of the lead body to the electrode positioned along the lead body, wherein the engaging portion corresponds to the second lead body lumen to provide an opening at the distal end of the lead body to receive the protruding member.

11. The medical electrical lead of claim 1, wherein the lead body further defines a second lead body lumen, wherein the at least one, electrode comprises a tip electrode at the distal end of the electrode head assembly electrically connected to the first conductor and a ring electrode more proximal thereto, and further wherein the medical electrical lead comprises a second conductor electrically connected to the ring electrode, wherein the second conductor extends across the joint through at least a portion of the second lead body lumen and through at least a portion of the electrode head assembly lumen.

12. The medical electrical lead of claim 1, further comprising a coil engaged with and about at least a portion of the lead body and about at least a portion of the body of the electrode head assembly across the joint, wherein the insulating member prevents current leakage between the first conductor and at least the coil.

13. A method for assembling a medical electrical lead, comprising the steps of:
    providing a lead body defining a first lead body lumen, the lead body extending between a distal end and a proximal end;
    providing an electrode head assembly comprising a body extending between a proximal end and a distal end, wherein the electrode head assembly comprises at least one electrode, wherein the body of the electrode head assembly defines an electrode bead assembly lumen;
    providing an insulating member extending from a proximal end to a distal end;
    inserting at least the distal end of the insulating member within the electrode head assembly lumen at the proximal end of the electrode head assembly;
    fixedly engaging the insulating member within the electrode head assembly lumen at the proximal end of the electrode head assembly, the insulating member electrically isolating a conductor;

inserting the proximal end of the insulating member within the first lead body lumen of the distal end of the lead body; and fixedly engaging the proximal end of the electrode head assembly and the distal end of the lead body.

14. The method of claim 13, wherein the insulating member is formed of PTFE.

15. The method of claim 13, further comprising the step of bonding a coil member to an outer portion of the lead body and an outer portion of the electrode head assembly and extending across the proximal end of the electrode assembly and the distal end of the lead body.

16. The method of claim 13, wherein the step of fixedly engaging further comprises inserting a protruding member extending from the proximal end of the electrode head assembly within an engaging portion located at the distal end of the lead body to align the electrode head assembly with the lead body.

* * * * *

UNITED STATES PATENT AND TRADEMARK OFFICE
CERTIFICATE OF CORRECTION

PATENT NO. : 8,219,211 B2  
APPLICATION NO. : 12/481216  
DATED : July 10, 2012  
INVENTOR(S) : Thomas C. Bischoff Page 1 of 1

It is certified that error appears in the above-identified patent and that said Letters Patent is hereby corrected as shown below:

In the Claims:

Col. 8, line 34, claim 11, delete "wherein the at least one, electrode" and insert in place thereof -- wherein the at least one electrode --;

Col. 8, line 58, claim 13, delete "bead assembly" and insert in place thereof -- head assembly --.

Signed and Sealed this  
Sixteenth Day of April, 2013

Teresa Stanek Rea  
*Acting Director of the United States Patent and Trademark Office*